US007066349B2

(12) United States Patent
Cohen

(10) Patent No.: US 7,066,349 B2
(45) Date of Patent: Jun. 27, 2006

(54) COMBINED TOOTHPICK AND MINT DISPENSER

(76) Inventor: Harris Cohen, 7337 Draper Ave., La Jolla, CA (US) 92126

( * ) Notice: Subject to any disclaimer, the term of this patent is extended or adjusted under 35 U.S.C. 154(b) by 0 days.

(21) Appl. No.: 10/949,255

(22) Filed: Sep. 27, 2004

(65) Prior Publication Data

US 2005/0155873 A1    Jul. 21, 2005

Related U.S. Application Data

(60) Provisional application No. 60/536,728, filed on Jan. 15, 2004.

(51) Int. Cl.
*B65G 59/00* (2006.01)
(52) U.S. Cl. .......................... 221/92; 206/38
(58) Field of Classification Search .................. 221/92, 221/34, 124, 199, 185; 206/216, 823, 528, 206/534.2, 538, 38, 37, 223; 220/524, 525, 220/554
See application file for complete search history.

(56) References Cited

U.S. PATENT DOCUMENTS

| 1,982,112 A | 11/1934 | Lang |
| 3,313,452 A | 4/1967 | Katz |
| 3,441,165 A | 4/1969 | Zampichelli |
| 3,773,215 A | 11/1973 | Makarevitz |
| 3,815,734 A | 6/1974 | Kruckel |
| 4,163,496 A * | 8/1979 | Dogliotti .................... 206/538 |
| 4,354,619 A | 10/1982 | Wippermann et al. |
| 5,249,674 A | 10/1993 | Lepie |
| 5,477,714 A * | 12/1995 | Bishop ........................ 70/459 |
| 5,513,774 A | 5/1996 | Dominquez |
| 6,247,595 B1 | 6/2001 | Omata et al. |
| 2004/0182877 A1* | 9/2004 | Oroumieh .................... 221/92 |

* cited by examiner

*Primary Examiner*—Kenneth Noland
(74) *Attorney, Agent, or Firm*—Hoffman, Wasson & Gitler

(57) ABSTRACT

A thin, plastic dispenser for discharging toothpicks, and/or mints through distinct discharge passages in the dispenser. The dispenser has a body comprising a first housing and a second housing that are aligned and snapped together to form the body of the dispenser. A well is defined in the body for storing toothpicks, and a first discharge passage is provided in the well. A larger chamber is defined in the body for storing mints, and a second discharge passage is provided in the chamber. Locking levers, integrally formed with one of the housings, normally seal the discharge passages in the well and the chamber. When the user wishes to discharge a toothpick and/or mint, the manually engages a locking lever and pivots same about its hinge line to expose the adjacent discharge passage. The contents of the well and/or chamber can then be discharged, through the exposed discharge passages vacated by the movement of the locking lever. Guides, ramps, and abutments in the well and chamber limit the width of the discharge passages and insure that the toothpicks are mints are discharged, one at a time, when the dispenser is tilted.

16 Claims, 5 Drawing Sheets

COMBINED TOOTHPICK AND MINT DISPENSER

This application claims priority based on provisional patent application Ser. No. 60/536,728, filed Jan. 15, 2004.

FIELD OF THE INVENTION

The invention pertains to a molded plastic dispenser that discharges mints and/or toothpicks, stored within the dispenser, through different discharge apertures, or openings, one at a time.

DESCRIPTION OF THE PRIOR ART

Various dispensers are known for dispensing mints, tablets, pills, and the like, stored within the interior of the dispenser. The dispenser must retain the product stored therein in a safe and dry environment, so that the mints, tablets, pills, etc. are not adversely influenced by ambient conditions, and retain a useful storage life that enables discharge of the product, in small quantities, over an extended period of time. Some of the known dispensers are discussed below.

To illustrate, U.S. Pat. No. 4,354,619, Wipperman et al disclose a flat container 1 comprising complementary housings 2, 3 adapted to be secured together to form a dispenser for tablets 4. Container 1 dispenses tablets, one at a time, by allowing same to pass through funnel shaped sorting trough 5 and into drop-out chamber 6, as shown in FIG. 3. Lower wall section 2' is then slid laterally to expose drop-out opening 18 which allows a single tablet to fall therethrough, as shown in FIGS. 3 and 4. Horizontal ribs 7 and 8, in the complementary housings slide relative t one another, to limit the size of the sorting trough; curved ramps or ledges 9, 10 on the ribs maintain the pills in the desired orientation as they enter the sorting trough. Spring blade 21 opposes the displacement of the housings relative to one another.

U.S. Pat. No. 3,773,215, Makarevitzu, discloses a dispenser for tablets, pills, candies, etc. in the form of a covered box 10. A portion 15 of the wall 13 of the box is resilient and deflectable inwardly to open, in combination with baffle 14, a dispensing opening, as shown in dotted outline in FIG. 3. Baffle 14 and interior wall 16 allow the discharge of one or more tablets, depending upon the size of the discharge opening, while retaining the remainder of the mints or candies in the dispenser.

U.S. Pat. No. 5,513,774, Dominguez, discloses a flat tablet dispenser comprising a bottom half 30 assuming the form of a rectangular tray, and a top half 10 having a complementary shape. Studs 21–25 are formed on the top half and fit into the sockets 41–45, on the bottom half. A hinged cap 50 controls the discharge of pills from the dispenser.

While diverse dispensers for pills, candies, tablets, etc. are known, dispensers for toothpicks are far from commonplace, particularly dispensers for discharging a single toothpick at a time. Toothpicks are usually sold, in relatively large quantities, in a paperboard box with a removable panel. Upon tearing the panel away, the contents of the box are exposed, and the toothpicks may be extracted, as needed. The contents of the box are susceptible of spilling out, if not properly handled. In some instances, smaller quantities of toothpicks are sold in metal tins. In both instances, no mechanism is provided for discharging the toothpicks one at a time, in a reliable manner, without spillage.

Combined dispensers for discharging individual toothpicks and/or mints, candies, pills, or the like, are not readily available.

Thus, it is a primary object of the instant invention to provide a combined toothpick and mint dispenser, capable of selectively dispensing toothpicks and/or mints, or candies, one at a time.

It is another object of the instant invention to provide a combined toothpick and mint dispenser capable of storing a large supply of toothpicks and mints, prior to discharge, in a sealed environment that keeps the toothpicks and mints isolated from dirt, lint, moisture, atmospheric conditions, etc. The toothpicks are stored in a well, while the mints are stored in a somewhat larger chamber; both the well and the chamber are defined within the interior of the body of the dispenser.

The toothpicks are discharged through a first discharge passage in the dispenser, while mints, candies, or the like are discharged through a second discharge passage. The passages are normally sealed by pivotally mounted locking levers. Each lever is pivoted away from its sealing position, as needed, to expose a discharge passage in the body of the dispenser.

Furthermore, it is another object of the invention to provide a dispenser comprised of an upper and lower housing, of generally rectangular shape, defined by upstanding end walls and side walls. Pins and receptacles are formed on opposing faces of the housings, so that the housings are aligned and then secured together. The locking levers fit into recesses on the opposing housing and assist in retaining the housings secured together. The dispenser is formed of a molded plastic that may be transparent or translucent, and may be colored, so that the resulting dispenser is aesthetically pleasing, and is thin or sleek enough to be carried in one's pocket or purse.

A clear-through aperture may be formed in one corner of the body of the dispenser. A split-ring may be slipped through the aperture, and a key chain may be joined to the split-ring so that the dispenser may be worn on a key chain.

SUMMARY OF THE INVENTION

The objects recited above, and other objects, are realized by the instant combined toothpick and mint dispenser which comprises a first housing and a second housing, with upstanding walls, and cooperating pins and receptacles that properly align the housings. After alignment, the two housings, which are generally rectangular in shape, are snapped or pressed together to form a sleek body for a dispenser that can fit easily into one's pocket or purse. The body may be formed of transparent or translucent plastic of different colors, so that the dispenser is esthetically pleasing, and may be embellished by the logo of the business, or person, distributing the combined dispenser.

Parallel, transverse walls extend between the end walls of one of the housings, and define the boundaries of a well adapted to receive a supply of toothpicks. An abutment in the well guides the toothpicks toward a first discharge passage in an end wall of the dispenser. A first locking lever, integrally formed with one of the housings and pivotable about a first hinge line, normally seals the discharge passage in the well.

A chamber is defined within the body of the dispenser to receive a supply of mints, candies, or the like. Ramps within the chamber guide the mints toward a second discharge opening. A second locking lever, integrally formed with one of the housings and pivotable about a second hinge line, normally seals the second discharge passage in the chamber. The locking levers also fit into recesses in the opposing housing to retain the body o the dispenser securely joined together, in addition to sealing the discharge passages.

Ramps, guides, and abutments, within the well and the chamber insure that only one toothpick and one mint are in position to be discharged at one time. Pivoting a locking lever about its hinge line, to expose the contents of the well and chamber, and then tilting the dispenser, allows the discharge of one toothpick and/or mint, at a time. The contents of the dispenser are not susceptible to inadvertent discharge or spillage.

DETAILED DESCRIPTION OF THE INVENTION

Figure 1:
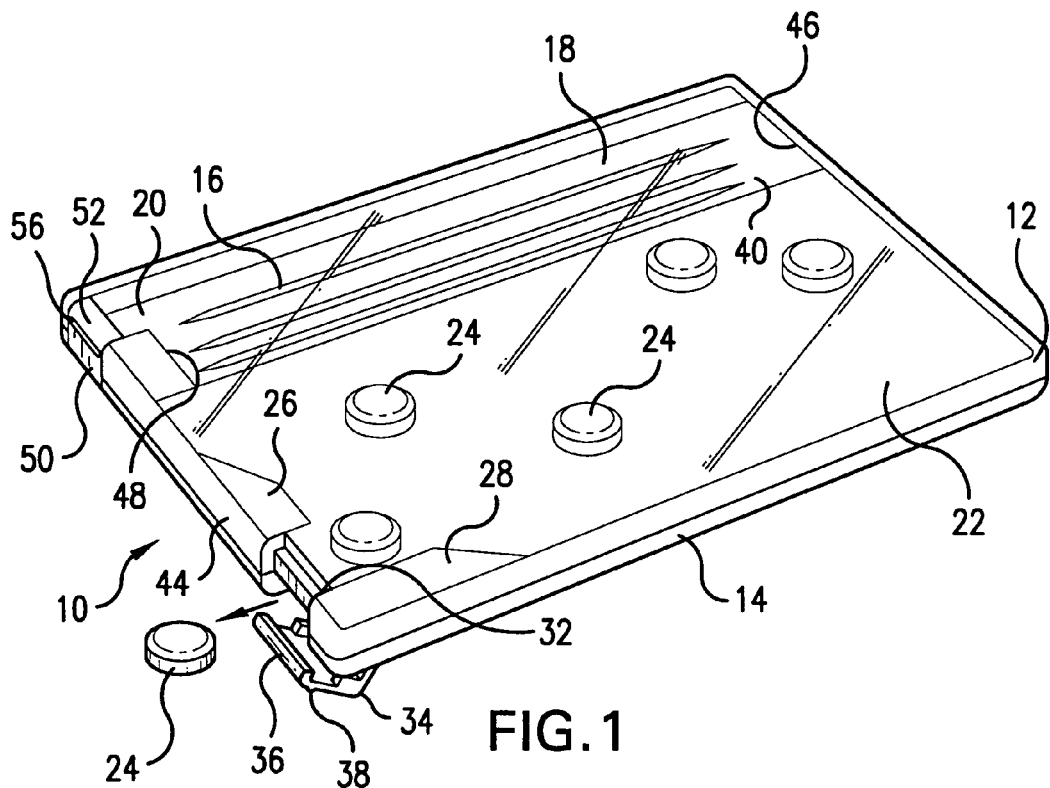
FIG. 1 is a perspective view of the preferred embodiment of a dispenser constructed in accordance with the principles of applicant's invention, such dispenser discharging a mint.
Figure 2:
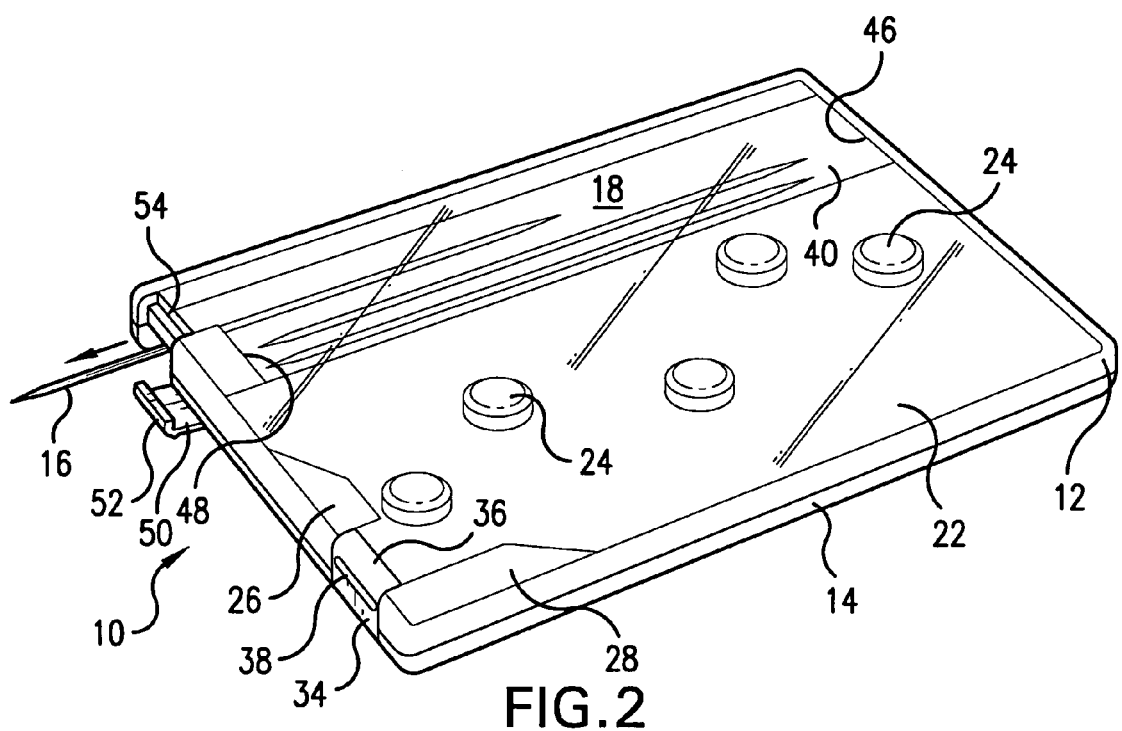
FIG. 2 is a perspective view similar to FIG. 1, but showing the dispenser discharging a toothpick.
Figure 3:
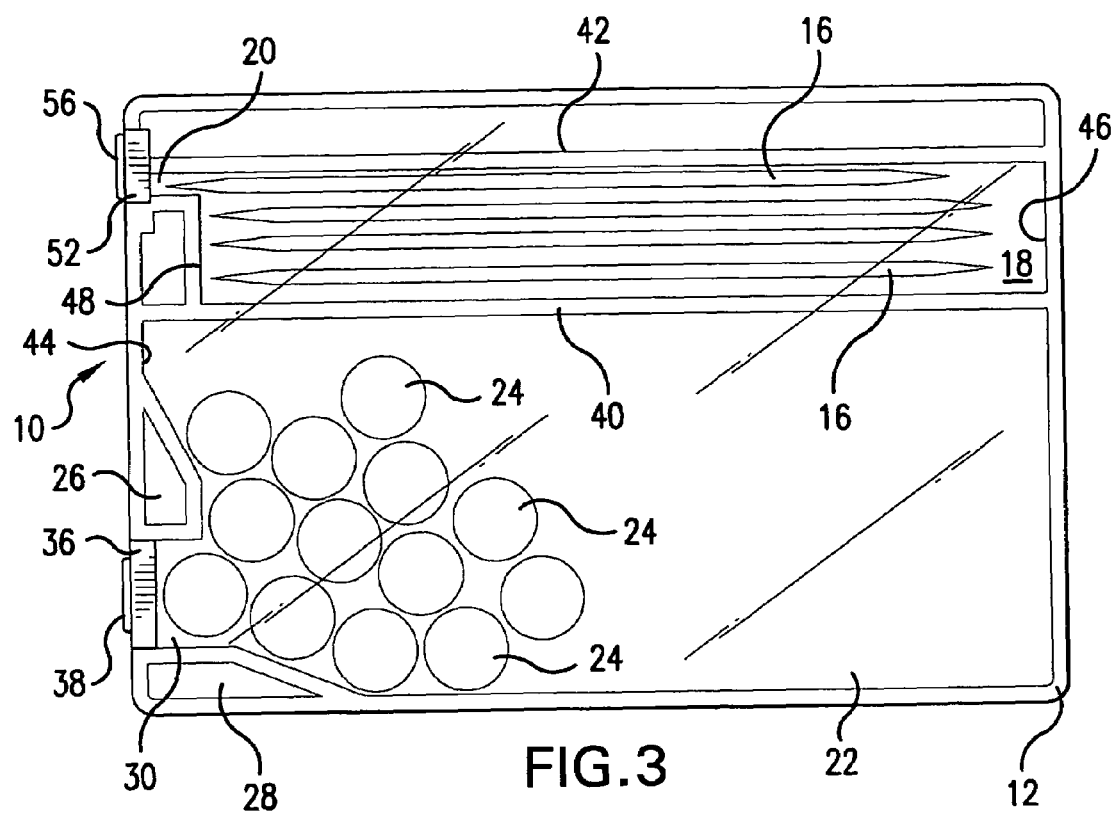
FIG. 3 is a top plan view of the dispenser of FIGS. 1 and 2.

FIGS. 1–3 depict dispenser 10, constructed in accordance with the principles of applicant's invention. Dispenser 10 comprises upper housing 12 and lower housing 14, which are joined together after proper alignment. The contents of container 10 can be observed through transparent, or translucent, housing 12. Housings 12 and 14 are substantially rectangular in shape, and may be formed from a colored plastic.

Toothpicks 16 are retained in well 18 defined within the interior of dispenser 10. Well 18 is substantially rectangular in shape, as shown in FIG. 3. Discharge passage 20 is situated in one side of well 18, and is sized to allow the discharge of one toothpick, at a time.

A larger, generally rectangular chamber 22 is also defined within the interior of housing 10. Mints 24, or similarly shaped candies, are stored within chamber 22. A first, vertically oriented ramp 26, directs mints 24 in vertical direction, while a second, horizontally oriented ramp 28, directs mints 22 in the horizontal, or lateral, direction across the vertical dimension of chamber 22. Discharge passage 30 is determined by the spacing between the lower edge of ramp 26 and the upper edge of ramp 28. The vertical dimension of discharge passage 30 is correlated with the diameter of mint 22 to be discharged.

Stepped ledge 32 is formed proximate to discharge opening 30. Locking lever 34, with projecting flange 36, normally seals discharge opening 30, for flange 36 is seated upon ledge 32. Nub 38 is engaged by the user's finger, or finger nail, when one wishes to expose discharge passage 30.

Well 18, which receives toothpicks 18, is rectangular in shape and stores several toothpicks. Well 18 is defined, in the lateral direction, by spaced, parallel internal walls 40, 42, and on its height dimension, by end walls 44, 46. Interior barrier 48 maintains the toothpicks in proper alignment. Discharge passage 20 is define between the upper surface of barrier 48 and interior wall 42, so that only one toothpick is in position to be discharged through passage 20, at any time.

Second locking lever 50 includes projecting flange 52 which usually engages ledges 54, to seal discharge opening 20. Discharge passages 20 and 30 are spaced along an end wall of the dispenser. Nib 56 is engaged by the user's finger, or finger nail, to pivot locking lever 50 out of engagement with ledge 54. The pivoted movement of locking lever 50 exposes opening 20 and allows the discharge of a single toothpick 16, as shown in FIG. 2.

FIGS. 4–8 show an alternative embodiment of applicant's unique dispenser. While the preferred embodiment of the dispenser may utilize upper and lower housings that are glued, welded or otherwise secured together, the alternative embodiment of the dispenser relies upon a series of cooperating pins and sockets to properly align the housings, and to permit same to be snapped together. Also, dispenser 110 may utilize a transparent upper housing, joined to a translucent lower housing, so that the contents of the dispenser may be readily observed. lastly, dispenser 110 is formed with a clear-through aperture in one corner; a key chain or ring may be passed through the aperture so that the dispenser 110 may be suspended from a belt, or key chain. The structural details of dispenser 110 may be gleaned from appended FIGS. 4–8.

Figure 4:
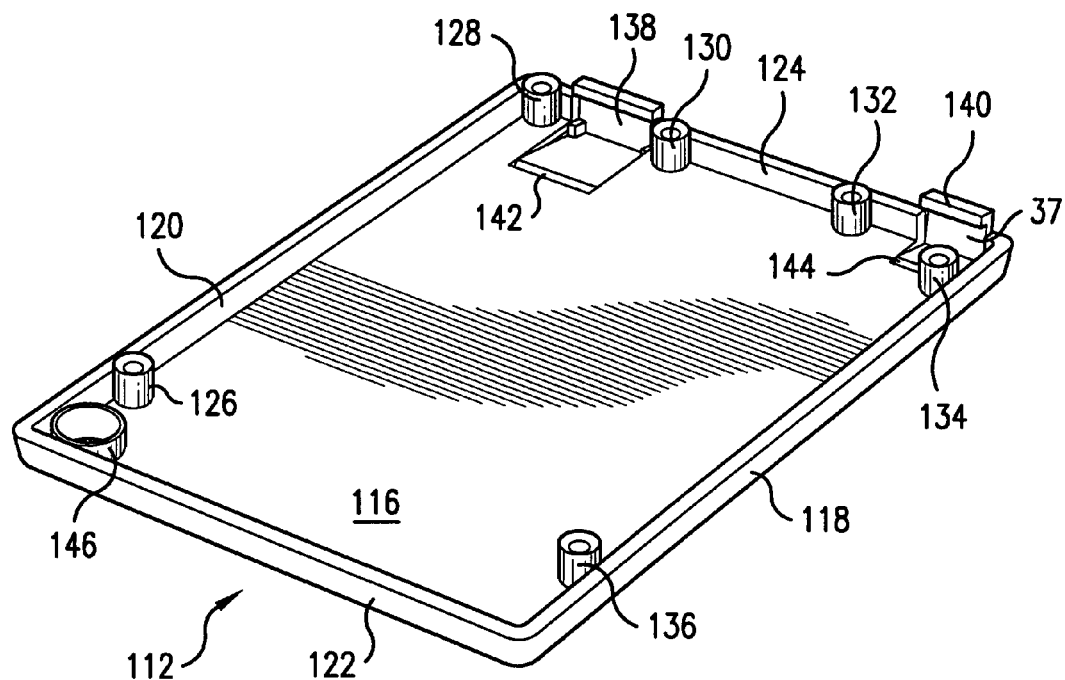
FIG. 4 is a perspective view of an alternate embodiment of the upper housing of applicant's dispenser.

As shown in FIG. 4, upper housing 112 of dispenser 110 comprises a planar base 116 surrounded by upstanding side walls 118, 120 and end walls 122, 124. Cylindrical sockets 126, 128, 130, 132, 134 and 136 are distributed about base 116 in proximity to the end walls and side walls, and extend upwardly above the end walls and side walls. Locking levers 138, 140 interrupt end wall 124 at spaced locations. Lever 138 is joined to base 116 along hinge line 142, while lever 140 is joined to base 116 along hinge line 144. Collar 146 is situated in the corner of base 116, proximate to the intersection of side wall 120 and end wall 122.

Figure 5:
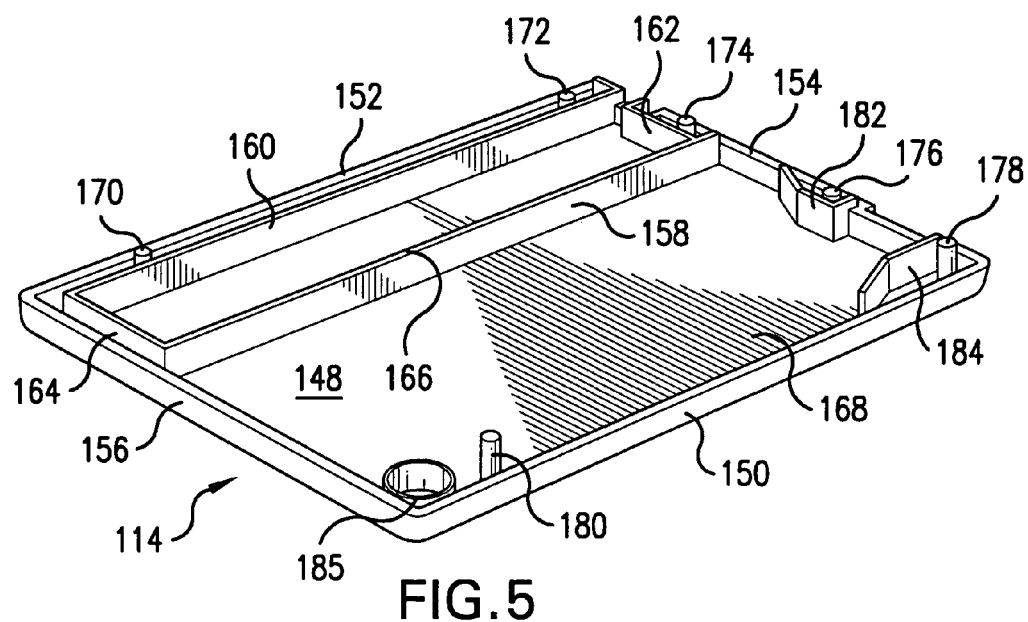
FIG. 5 is a perspective view of an alternate embodiment of the lower housing of applicant's dispenser.

As shown in FIG. 5, lower housing 114 comprises a planar base 148 surrounded by upstanding side walls 150, 152 and end walls 154, 156. Interior walls 158, 160 and spaced transverse walls 162, 164 define rectangular well 166 within the confines of housing 114. Well 166 is adapted to toothpicks or similar slender articles.

Chamber 168, which is rectangular in shape and larger than well 166, is situated adjacent thereto. Side wall 150, end walls 154, 156, interior wall 148, and base 148 define the dimensions of chamber 168.

Pins 170, 172, 174, 176, 178 and 180 are distributed about base 148 of housing 114 in a pattern corresponding to the distribution of the sockets on housing 112. First vertical ramp 182 is situated within chamber 168 in proximity to pin 176, while second horizontal ramp 184 is situated within chamber 148 in proximity to pin 178.

Ramps 182, 184 extend upwardly above end wall 154 and are separated by a distance slightly greater than the diameter of the mints or candies stored in chamber 168. Collar 185 is located in a corner of housing 114.

Figure 6:
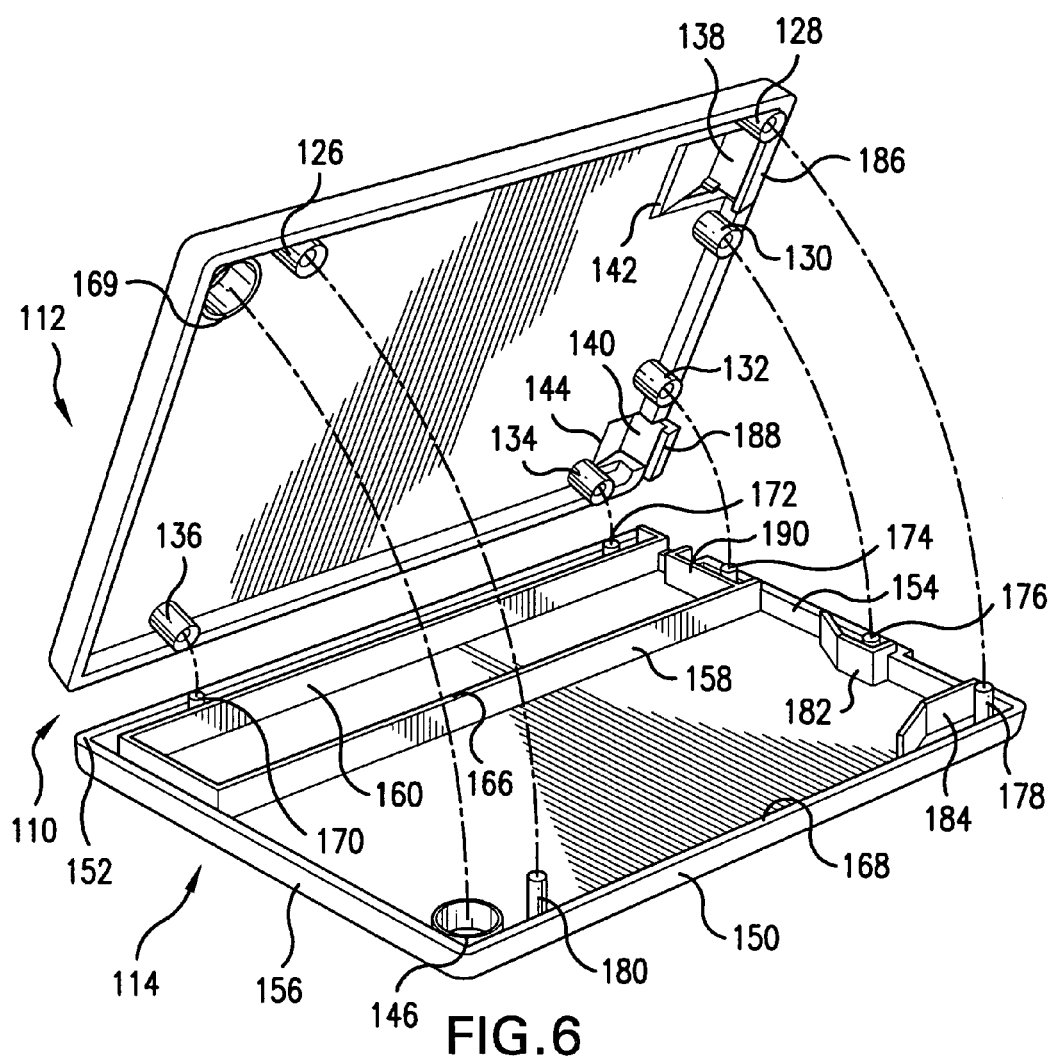
FIG. 6 is an exploded perspective view showing the upper and lower housings of FIGS. 4 and 5 being joined together.

FIG. 6 shows housing 112 being joined to, or secured to, housing 114. Sockets 126, 128, 130, 132, 134 and 136 are brought into engagement with pins 170, 172, 174, 176, 178 and 180 or vice versa. The interaction between the pins and the sockets aligns housings 112 and 114. Collars 146, 185 are also aligned.

Side walls 118, 120 and end walls 112, 124 of housing 112 rest upon end walls 150, 152 and side walls 154, 156 of housing 114. Projecting flange 186 on locking lever 138 snaps into a recess (not shown) in housing 114, while projecting flange 188 on locking lever 140 snaps into a recess (now shown) adjacent discharge opening 82, in the end wall 154 of chamber 168. The engagement of projecting flanges 186, 188 in recesses, or upon the ledges, of housing 114 snaps the housings 112, 114 together to define the body of dispenser 110. Collars 146, 185 are pressed together in line-to-line contact so that dust, pocket line, etc. can not gain entry to chamber 168 and adversely impact upon the mints, candies, etc. stored therein.

After the assembly process shown in FIGS. 4–6 is completed, dispenser 110 assumes the same form shown in FIGS. 1–3. Toothpicks are retained in well 166. The distance between transverse interior barrier 190 and transverse wall 160, which defines the first discharge passage, is selected so that only one toothpick may fit therein and be discharged therefrom. Locking lever 138 normally blocks the outer end of the discharge passage for toothpicks. However, when locking lever 138 is pivoted out of the way by the user, one toothpick at a time, may be discharged through the discharge passage. The adjacent toothpick in the well is advanced into the discharge passage by tilting the body of the dispenser. After the desired number of toothpicks has been discharged, locking lever 136 is pivoted about hinge line 142 into locking engagement with housing 114 to seal the discharge passage. Toothpicks are not shown in FIGS. 4–6, but are identified by reference numeral 16 in FIGS. 1–3.

Mints are not shown in FIGS. 4–6; however, mints 24 are shown in FIGS. 1–3 and are stored in chamber 62 within the body of dispenser 10. Ramps 182, 184 guide the mints toward a discharge passage in chamber 166. The distance between the rams is selected so that only one mint at a time can fit into the discharge passage and pass over side wall 154. Locking lever 138 normally blocks the discharge passage leading from chamber 168. However, when the user desires a mint, he, or she, pivots lever 138 about hinge 142 and allow a mint to pass through the discharge passage. The mints are discharged, one at a time, by tilting the dispenser 10 so that the mints clear the end wall of the housing of dispenser 110.

Figure 7:
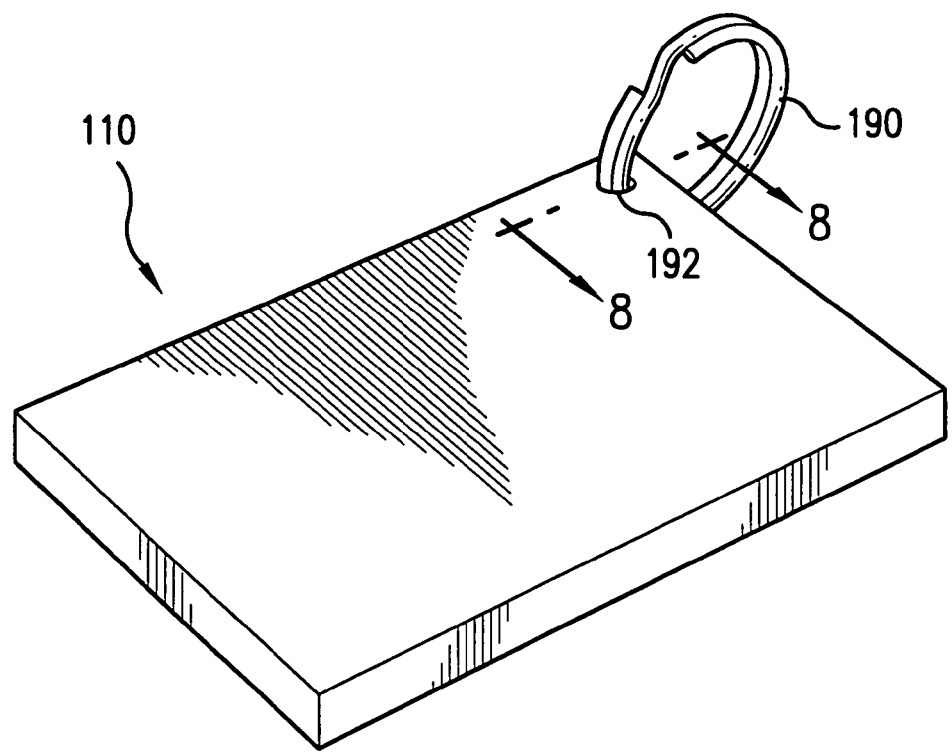
FIG. 7 is a perspective view of the alternative embodiment of applicant's dispenser, wherein a slip ring is passed through a bore in the dispenser body.
Figure 8:
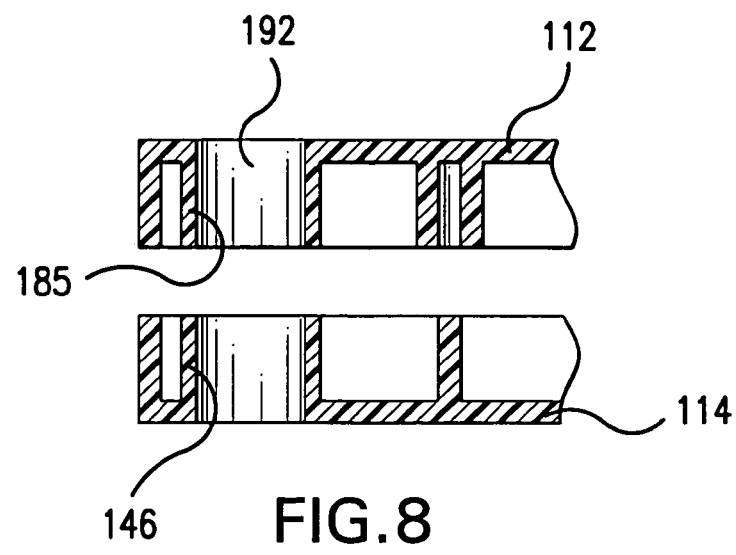
FIG. 8 is a partial, vertical cross-sectional view of the dispenser of FIG. 7, such view being taken along line 8—8 in FIG. 7 and in the direction indicated.

FIGS. 7 and 8 show that split ring 190 may be passed through bore 192 formed by the engagement of collars 146 and 169 in one corner of dispenser 110. A chain may be passed through bore 192, in lieu of a split ring, or the chain may be used in combination with the split ring. Dispenser 110 may be worn on a key chain, or positioned about a belt, or retained in a pocket or purse.

Numerous modifications and revisions may occur to the artisan from the description set forth above. For example, the locking levers may define discharge openings in the end walls or side walls of the dispenser. Other mechanical arrangements may be used to join the first and second housings together. Diverse plastics may be used. Consequently, the appended claims should be broadly construed in a fashion consistent with the spirit and scope of applicant's unique invention, and should not be limited to their literal terms.

| PARTS LIST - FIGS. 1–3 | |
|---|---|
| 10 | dispenser (general) |
| 12 | upper housing |
| 14 | lower housing |
| 16 | toothpicks |
| 18 | well |
| 20 | discharge passage in well |
| 22 | rectangular chamber |
| 24 | mints |
| 26 | first, vertically oriented ramp |
| 28 | second, horizontally oriented ramp |
| 30 | discharge passage in chamber |
| 32 | ledge |
| 34 | first locking lever |
| 36 | projecting flange on lever 34 |
| 38 | nub |
| 40/42 | spaced, parallel internal walls for well 18 |
| 44/46 | end walls |
| 48 | interior barrier |
| 50 | second locking lever |
| 52 | projecting flange on lever 50 |
| 54 | ledge |

| PARTS LIST - FIG. 4 ALTERNATIVE EMBODIMENT - DISPENSER 110 | |
|---|---|
| 112 | upper housing |
| 116 | planar base |
| 118/120 | side walls |
| 122/124 | end walls |
| 126, 128, 130, 132, 134 & 136 | cylindrical sockets |
| 138, 140 | locking levers |
| 142 | hinge line for lever 138 |
| 144 | hinge line for lever 140 |
| 146 | collar |

| PARTS LIST - FIG. 5 | |
|---|---|
| 114 | lower housing |
| 148 | planar base |
| 150/152 | side walls |
| 154/156 | end walls |
| 158/160 | interior walls |
| 162/164 | transverse walls |
| 166 | rectangular well |
| 168 | chamber |
| 170, 172, 174, 176, 178 & 180 | pins on base 148 |
| 182 | first vertical ramp |
| 184 | second horizontal ramp |
| 185 | collar |

| PARTS LIST - FIG. 6 | |
|---|---|
| 186 | flange on locking lever 138 |
| 188 | flange on locking lever 140 |

| PARTS LIST - FIGS. 7 and 8 | |
|---|---|
| 190 | slip ring |
| 192 | bore |

I claim:

1. A combined toothpick and mint dispenser comprising:
 a) a first housing including a planar base,
 b) spaced end walls and spaced side walls projecting from said base of said first housing an extending around the perimeter of said base,
 c) a second housing including a planar base,
 d) spaced end walls and spaced side walls projecting from said base of said second housing and extending around the perimeter of said base,
 e) said first and second housings joined together along said end walls and said side walls to form the body of said dispenser,
 f) a well defined within said body, said well adapted to receive and retain toothpicks therein,
 g) a first discharge passage in said well for allowing toothpicks to pass there through, to the exterior of said body,
 h) a first locking lever for normally sealing the first discharge passage,
 i) a chamber defined within said body, said chamber adapted to receive and retain mints therein,
 j) a second discharge passage in said chamber for allowing mints to pass therethrough to the exterior of said body,
 k) a second locking lever, integrally formed with one of said housings, for normally sealing the second discharge passage,
 l) said first and second locking levers being pivoted out of sealing engagement with said discharge passages to allow the contents of the well and chamber to be discharged there through upon tilting the dispenser.

2. A combined toothpick and mint dispenser as defined in claim 1, wherein said locking levers are integrally formed with one of said housings and are pivotable about hinge lines formed in said planar base of one of said housings.

3. A combined toothpick and mint dispenser as defined in claim 2, wherein each of said locking levers terminates, at the end remote from its hinge line, in a projecting flange.

4. A combined toothpick and mint dispenser as defined in claim 3, wherein recesses are formed in the body of said dispenser to receive said projecting flanges and retain said housings in joined condition.

5. A combined toothpick and mint dispenser as defined in claim 1, wherein said housings are substantially rectangular in shape.

6. A combined toothpick and mint dispenser as defined in claim 1, wherein said well is formed in one of said housings by a pair of spaced, parallel transversely extending interior walls and a pair of spaced end walls, said interior walls and said end walls defining a well of rectangular shape.

7. A combined toothpick and mint dispenser as defined in claim 6, wherein barrier means are located within said well to limit the width of said first discharge passage and allow only one toothpick at a time to enter said first discharge passage.

8. A combined toothpick and mint dispenser as defined in claim 7, wherein said barrier means comprises an abutment extending from one of said transverse walls toward the other of said transverse walls.

9. A combined toothpick and mint dispenser as defined in claim 1, wherein said chamber is formed in one of said housings, said chamber being rectangular in shape and larger in size than said well, said chamber and said well being formed in the same housing.

10. A combined toothpick and mint dispenser as defined in claim 1, wherein barriers are located within said chamber to limit the width of said second discharge opening, and allow only one mint at a time to enter said second discharge passage.

11. A combined toothpick and mint dispenser as defined in claim 10, wherein said barrier means comprises a pair of spaced ramps, said ramps guiding the mints toward said second discharge opening when said dispenser is tilted.

12. A combined toothpick and mint dispenser as defined in claim 1, wherein pins on one of said housings cooperates with sockets on the other said housings to align said housing prior to joining same together.

13. A combined toothpick and mint dispenser as defined in claim 1, wherein a first cylindrical collar is formed in said first housing, and a second, cylindrical collar is formed in said second housing, said collars contacting each other when said housings are joined together, said collars forming a bore through the body of said dispenser.

14. A combined toothpick and mint dispenser as defined in claim 13, wherein said collars contact each other in line-to-line contact to define a bore that is isolated from said chamber, said bore being adapted to receive a split-ring therein.

15. A combined toothpick and mint dispenser as defined in claim 1 wherein said first discharge passage is located in one of said end walls, and said second discharge opening is located in one of said side walls.

16. A combined toothpick and mint dispenser as defined in claim 15 wherein said first and second discharge passages are located at the same side of said dispenser.

* * * * *